(12) United States Patent
Blumenkranz et al.

(10) Patent No.: US 8,945,095 B2
(45) Date of Patent: *Feb. 3, 2015

(54) FORCE AND TORQUE SENSING FOR SURGICAL INSTRUMENTS

(75) Inventors: Stephen J. Blumenkranz, Redwood City, CA (US); David Q. Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1760 days.

This patent is subject to a terminal disclaimer.

(21) Appl. No.: 11/537,241

(22) Filed: Sep. 29, 2006

(65) Prior Publication Data

US 2007/0151390 A1 Jul. 5, 2007

Related U.S. Application Data

(60) Provisional application No. 60/755,108, filed on Dec. 30, 2005.

(51) Int. Cl.
*A61B 1/00* (2006.01)
*A61B 19/00* (2006.01)
(Continued)

(52) U.S. Cl.
CPC ......... *A61B 19/2203* (2013.01); *A61B 1/00059* (2013.01); *A61B 17/29* (2013.01); *A61B 19/46* (2013.01); *A61B 19/5225* (2013.01); *A61B 2017/2927* (2013.01); *A61B 2019/2223* (2013.01); *A61B 2019/223* (2013.01); *A61B 2019/2234* (2013.01); *A61B 2019/2242* (2013.01); *A61B 2019/2292* (2013.01); *A61B 2019/464* (2013.01); *A61B 2019/465* (2013.01); *A61B 2019/466* (2013.01); *A61B 2019/5261* (2013.01); *A61B 2562/0266* (2013.01); *B25J 15/0009* (2013.01)
USPC ............................................................ 606/1

(58) Field of Classification Search
USPC .................................................. 606/1, 41–52
See application file for complete search history.

(56) References Cited

U.S. PATENT DOCUMENTS

| | | | |
|---|---|---|---|
| 3,515,137 A | 6/1970 | Santomieri | |
| 4,838,280 A | 6/1989 | Haaga | |

(Continued)

FOREIGN PATENT DOCUMENTS

| | | | |
|---|---|---|---|
| EP | 1650615 A1 | 4/2006 | |
| FR | 2693397 A1 | 1/1994 | |

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.
PCT/US06/61994 International Search Report and Written Opinion of the International Searching Authority, mailed Oct. 17, 2007, 9 pages.
Cepolina F. et al., "Review of robotic fixtures for minimally invasive surgery," International Journal of Medical Robotics and Computer Assisted Surgery, 2004, pp. 43-63, vol. 1, Issue-1.
PCT/US08/76123 International Search Report and Written Opinion of the International Search Authority, mailed May 19, 2009, 15 pages.
"PCT/US08/76123 Partial International Search Report, mailed Jan. 12, 2009, 3 pages".

(Continued)

*Primary Examiner* — Aaron Roane

(57) ABSTRACT

An apparatus, system, and method for improving force and torque sensing and feedback to the surgeon performing a telerobotic surgery are provided. Groups of axially oriented strain gauges are positioned on a distal end of an instrument shaft proximate a moveable wrist of a robotic surgical instrument to sense forces and torques at the distal tip of the instrument. Advantageously, errors due to changes in the configuration of the tip or steady state temperature variations are eliminated. Other advantageous configurations and methods are disclosed.

41 Claims, 10 Drawing Sheets

(51) Int. Cl.
B25J 15/00 (2006.01)
A61B 17/29 (2006.01)

(56) References Cited

U.S. PATENT DOCUMENTS

| | | | |
|---|---|---|---|
| 4,906,907 | A | 3/1990 | Tsuchihashi et al. |
| 5,779,697 | A | 7/1998 | Glowa et al. |
| 5,784,542 | A | 7/1998 | Ohm et al. |
| 5,807,326 | A | 9/1998 | O'Neill et al. |
| 6,120,433 | A * | 9/2000 | Mizuno et al. ............... 600/102 |
| 6,206,835 | B1 | 3/2001 | Spillman, Jr. et al. |
| 6,344,038 | B1 | 2/2002 | Weber |
| 6,470,205 | B2 | 10/2002 | Bosselmann et al. |
| 6,494,882 | B1 | 12/2002 | Lebouitz et al. |
| 6,574,355 | B2 | 6/2003 | Green |
| 6,587,750 | B2 | 7/2003 | Gerbi et al. |
| 6,594,552 | B1 | 7/2003 | Nowlin et al. |
| 6,810,750 | B1 | 11/2004 | Kiefer et al. |
| 6,835,173 | B2 * | 12/2004 | Couvillon, Jr. ............... 600/146 |
| 7,357,774 | B2 | 4/2008 | Cooper |
| 7,606,615 | B2 | 10/2009 | Makower et al. |
| 7,648,513 | B2 | 1/2010 | Green et al. |
| 7,678,075 | B2 | 3/2010 | Wantink et al. |
| 7,824,401 | B2 | 11/2010 | Manzo et al. |
| 7,842,028 | B2 | 11/2010 | Lee |
| 8,004,229 | B2 | 8/2011 | Nowlin et al. |
| 8,375,808 | B2 | 2/2013 | Blumenkranz et al. |
| 8,613,230 | B2 | 12/2013 | Blumenkranz et al. |
| 8,628,518 | B2 | 1/2014 | Blumenkranz et al. |
| 2002/0111635 | A1 | 8/2002 | Jensen et al. |
| 2002/0133174 | A1 | 9/2002 | Charles et al. |
| 2003/0036748 | A1 * | 2/2003 | Cooper et al. ................ 606/1 |
| 2003/0229286 | A1 * | 12/2003 | Lenker ......................... 600/462 |
| 2005/0021050 | A1 | 1/2005 | Cooper et al. |
| 2006/0161136 | A1 | 7/2006 | Anderson et al. |
| 2006/0161137 | A1 | 7/2006 | Orban, III |
| 2006/0235436 | A1 | 10/2006 | Anderson et al. |
| 2007/0078484 | A1 | 4/2007 | Talarico et al. |
| 2007/0119274 | A1 | 5/2007 | Devengenzo et al. |
| 2007/0137371 | A1 | 6/2007 | Devengenzo et al. |
| 2007/0151391 | A1 | 7/2007 | Larkin et al. |
| 2007/0156019 | A1 | 7/2007 | Larkin et al. |
| 2008/0065111 | A1 | 3/2008 | Blumenkranz et al. |
| 2014/0100588 | A1 | 4/2014 | Blumenkranz et al. |
| 2014/0107627 | A1 | 4/2014 | Blumenkranz et al. |

FOREIGN PATENT DOCUMENTS

| | | |
|---|---|---|
| JP | H06142114 A | 5/1994 |
| JP | H08224246 A | 9/1996 |
| JP | 9318469 A | 12/1997 |
| JP | 2002159509 A | 6/2002 |
| JP | 27167644 A2 | 7/2007 |
| WO | WO-9825666 A1 | 6/1998 |
| WO | WO 2005-039835 A | 5/2005 |
| WO | 2007120329 A2 | 10/2007 |
| WO | WO-2007111737 A2 | 10/2007 |

OTHER PUBLICATIONS

Seibold, Ulrich et al., "A 6-axis force/torque sensor design for haptic feedback in minimally invasive robotic surgery," In: Proceedings of the 2nd VDE World Microtechnologies, 2003, 6 Pages.
Anagnostou, D, et al., "Improved Multiband Performance with Self-Similar Fractal Antennas", IEEE Topical Conference on Wireless Communication Technology, Oct. 15-17, 2003, pp. 271-272, IEEE.
Brocato, Robert W., "Passive Wireless Sensor Tags" Sandia Report, Mar. 2006, pp. 1-20, Sandia National Laboratories, Albuquerque, NM, USA.
Fractus' Micro Reach XtendT 2.4GHz Antenna Sets New Standard for Antenna Miniaturisation, Fractus News, Mar. 6, 2007, pp. 1-2 [online], Fractus S.A., Retrieved on Jul. 9, 2010 from the Internet: <URL:http://www.fractus.com/main/fractus/news_english/fractus_micro_reach_xtend_24ghz_antenna_sets_new_standard_for_antenna_minia/>. No author provided.
Fractus® Reach XtendT Chip Antenna, Data Sheet—Products & Services, 2007, 2 pages, Fractus S.A. No author provided.
Jones, Inke, et al, "Wireless RF Communication in Biomedical Applications", Smart Materials and Structures, 2008, 17 (1), IOP Publishing Ltd., UK, pp. 1-10.
Lonsdale A., "Dynamic Rotary Torque Measurement Using Surface Acoustic Waves", Sensors, Oct. 2001, 18 (10), Sensor Technology Ltd., UK, 51-56.
McDonald et al., "Small Fractal Antennas Princeton University, Princeton, NJ, USA. Retrieved from the Internet: <URL:http://www.hep.princeton.edu/~mcdonald/examples/fractal_antenna.pdf>.", Dec. 22, 2003, Princeton University, Princeton, NJ, USA., pp. 1-9.
Nomura T., et al., "Wireless Passive Strain Sensor Based on Surface Acoustic Wave Devices", Sensors & Transducers journal, Apr. 15, 2008, 90, International Frequency Sensor Association Publishing, 61-71.
Pohl, et al., "A Review of Wirelest SAW Sensors IEEE Transactions on Ultrasonics, Ferroelectrics, and Frequency Control,", Mar. 2000, 47 (2), IEEE, 317-332.
Reindl, et al., "SAW-Based Radio Sensor Systems", IEEE Sensors Journal, Jun. 2001, 1 (1), IEEE, 69-78.
Reindl, et al., "Theory and Application of Passive SAW Radio Transponders as Sensors", IEEE Transactions on Ultrasonics, Ferroelectrics, and Frequency Control, Sep. 1998, 45 (50, 1281-1292.
Scholl G., et al., "SAW-Based Radio Sensor Systems for Short-Range Applications", IEEE Microwave Magazine, Dec. 2003, IEEE., 68-76.
Sherrit, et al., "BAW and SAW Sensors for In-Situ Analysis", Proceedings of the SPIE Smart Structures Conference San Diego, CA, Mar. 2-6, 2003, 5050 (11), SPIE, 11 pages.
Wang, et al., "Optimal Design on SAW Sensor for Wireless Pressure Measurement Based on Reflective Delay Line", Sensors and Actuators A: Physical, Sep. 12, 2007, 139 (1-2), Elsevier B.V., pp. 2-6.

* cited by examiner

FORCE AND TORQUE SENSING FOR SURGICAL INSTRUMENTS

CROSS-REFERENCE TO RELATED APPLICATIONS AND PATENTS

This application claims priority to and the benefit of U.S. Provisional Application No. 60/755,108, filed Dec. 30, 2005, the full disclosure of which (including all references incorporated by reference therein) is incorporated by reference herein for all purposes.

This application is related to U.S. patent application Ser. No. 11/093,372 filed Mar. 30, 2005 (US20050200324 A1, published Sep. 15, 2005), and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which (including all references incorporated by reference therein) are incorporated by reference herein for all purposes.

TECHNICAL FIELD

The present invention relates generally to surgical robot systems and, more particularly, to a system and method for sensing forces applied to a surgical instrument.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves inserted through incisions into a body cavity, such as the patient's abdomen. Depending on the surgical procedure, there are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, or dissecting, cauterizing or coagulating tissue. A surgeon may employ a large number of different surgical instruments/tools during a procedure.

This new method of performing telerobotic surgery through remote manipulation has, of course, created many new challenges. One such challenge is providing the surgeon with the ability to accurately "feel" the tissue that is being manipulated by the surgical instrument via the robotic manipulator. The surgeon must rely on visual indications of the forces applied by the instruments or sutures. It is desirable to sense the forces and torques applied to the tip of the instrument, such as an end effector (e.g., jaws, grasper, blades, etc.) of robotic endoscopic surgical instruments, in order to feed the forces and torques back to the surgeon user through the system hand controls or by other means such as visual display or audible tone. One device for this purpose from the laboratory of G. Hirzinger at DLR is described in "Review of Fixtures for Low-Invasiveness Surgery" by F. Cepolina and R C Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires for mechanical actuation of end effectors in as small a space as possible as relatively small instruments are typically desirable for performing surgery.

What is needed, therefore, are improved telerobotic systems and methods for remotely controlling surgical instruments at a surgical site on a patient. In particular, these systems and methods should be configured to provide accurate feedback of forces and torques to the surgeon to improve user awareness and control of the instruments.

SUMMARY

The present invention provides an apparatus, system, and method for improving force and torque feedback to and sensing by the surgeon performing a telerobotic surgery. Groups of axially oriented strain gauges are positioned on or near a distal end of an instrument shaft proximal to (or inboard of) a moveable wrist of a robotic surgical instrument to sense forces and torques at the distal tip of the instrument without errors due to changes in the configuration of the tip (such as with a moveable wrist) or steady state temperature variations.

Advantageously, the present invention improves the sensing and feedback of forces and/or torques to the surgeon and substantially eliminates the problem of passing delicate wires through the flexible wrist joint of the instrument.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1A:
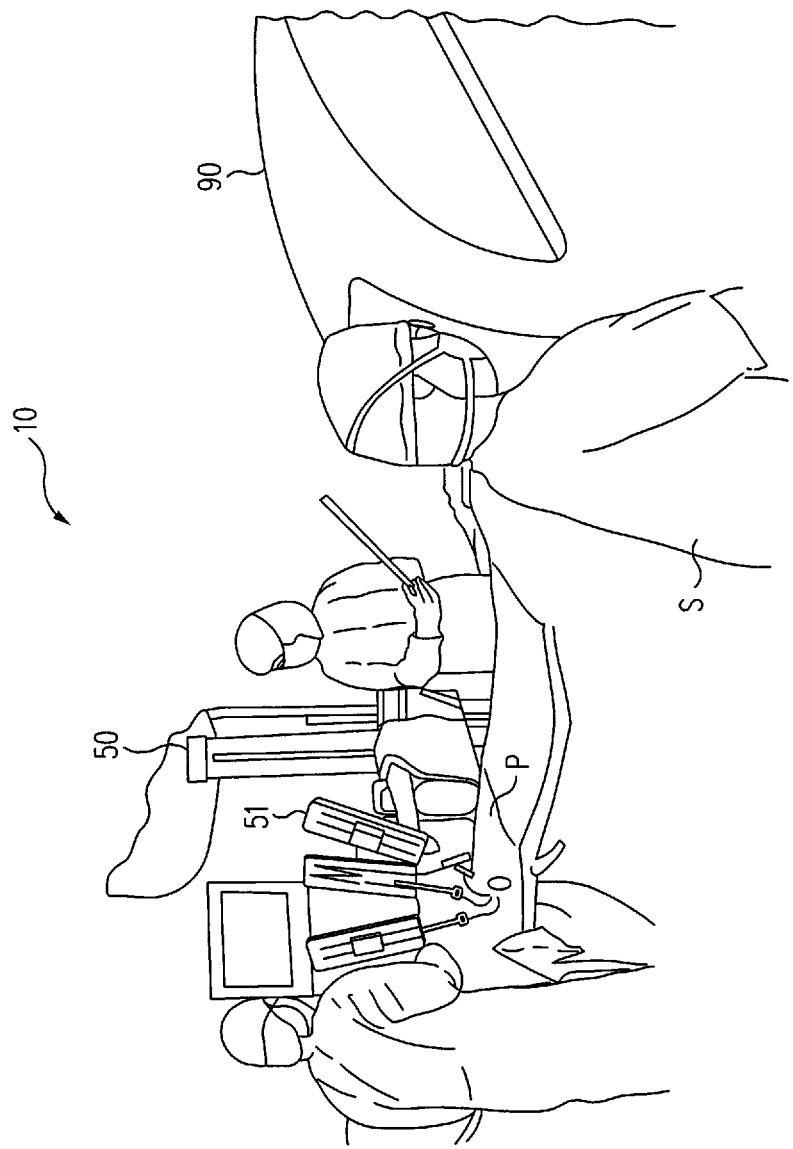
FIG. 1A is a perspective view of a robotic surgical system and method in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces applied to tissue while performing robotically-assisted surgical procedures on a patient, particularly including open surgical procedures, neurosurgical procedures, such as stereotaxy, and endoscopic procedures, such as laparoscopy, arthroscopy, thoracoscopy and the like. The system and method of the present invention is particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master having six or more degrees of freedom (e.g., 3 degrees of freedom for position and 3 degrees of freedom for orientation) to form a telepresence system with force reflection. A description of a suitable slave-master system can be found in U.S. patent application Ser. No. 08/517,053, filed Aug. 21, 1995, the complete disclosure of which is incorporated herein by reference for all purposes.

Figure 1B:
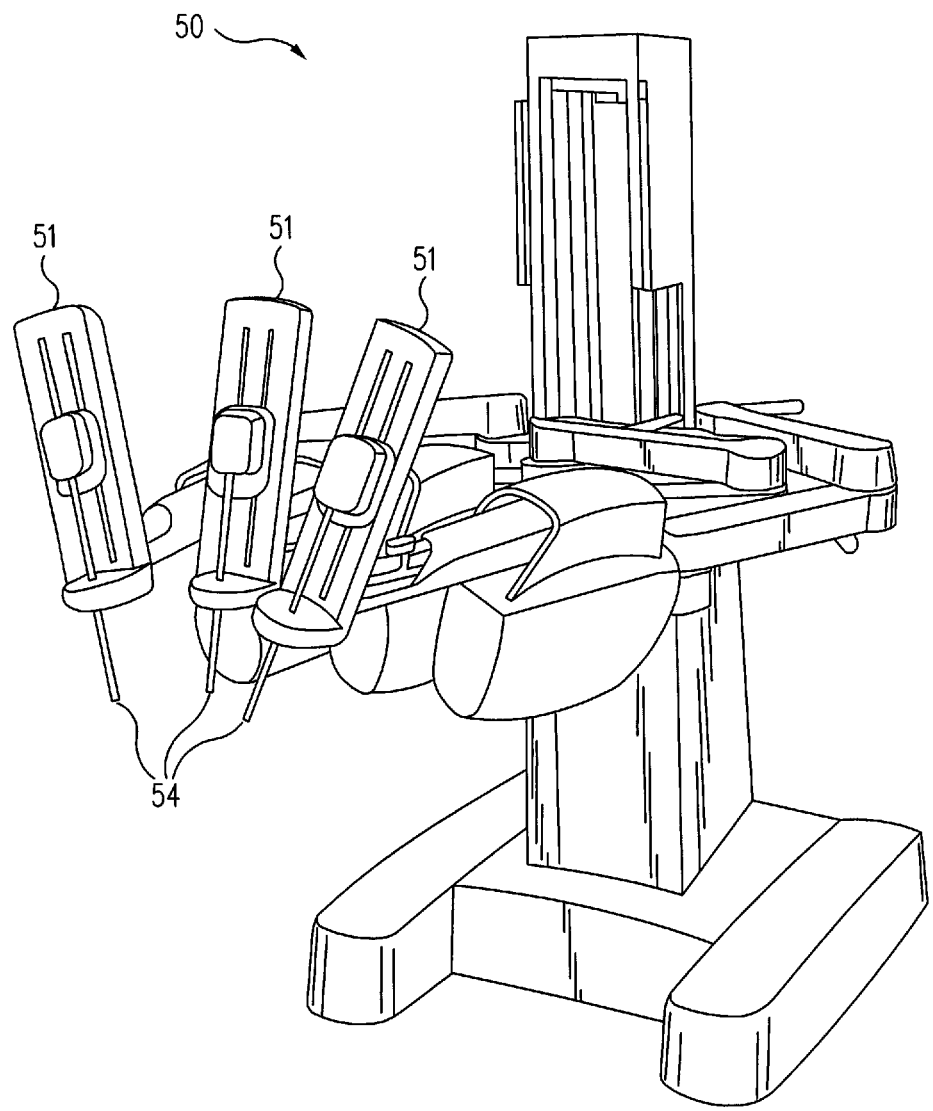
FIG. 1B is a perspective view of a robotic surgical arm cart system of the robotic surgical system in FIG. 1A in accordance with an embodiment of the present invention.
Figure 1C:
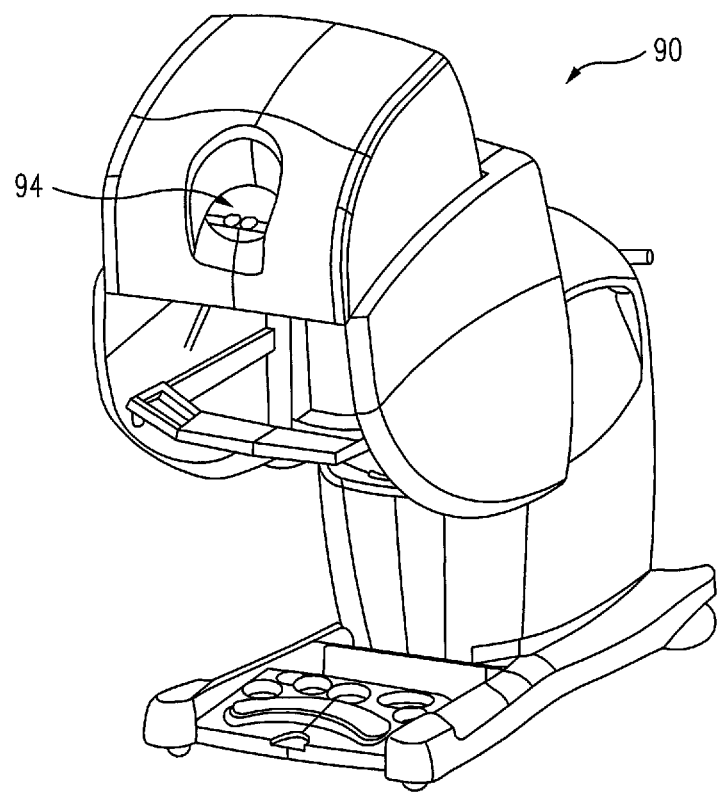
FIG. 1C is a front perspective view of a master console of the robotic surgical system in FIG. 1A in accordance with an embodiment of the present invention.

Referring to the drawings in detail, wherein like numerals indicate like elements, a robotic surgical system 10 is illustrated according to an embodiment of the present invention. As shown in FIGS. 1A through 1C, robotic system 10 generally includes one or more surgical manipulator assemblies 51 mounted to or near an operating table, and a master control assembly 90 for allowing the surgeon S to view the surgical site and to control the manipulator assemblies 51. The system 10 will also include one or more viewing scope assemblies and a plurality of surgical instrument assemblies 54 adapted for being removably coupled to the manipulator assemblies 51 (discussed in more detail below). Robotic system 10 usually includes at least two manipulator assemblies 51 and preferably three manipulator assemblies 51. The exact number of manipulator assemblies 51 will depend on the surgical procedure and the space constraints within the operating room among other factors. As discussed in detail below, one of the assemblies 51 will typically operate a viewing scope assembly (e.g., in endoscopic procedures) for viewing the surgical site, while the other manipulator assemblies 51 operate surgical instruments 54 for performing various procedures on the patient P.

Control assembly 90 may be located at a surgeon's console which is usually located in the same room as operating table 0 so that the surgeon may speak to his/her assistant(s) and directly monitor the operating procedure. However, it should be understood that the surgeon S can be located in a different room or a completely different building from the patient P. Master control assembly 90 generally includes a support, a monitor for displaying an image of the surgical site to the surgeon S, and one or more master(s) for controlling manipulator assemblies 51. Master(s) may include a variety of input devices, such as hand-held wrist gimbals, joysticks, gloves, trigger-guns, hand-operated controllers, voice recognition devices or the like. Preferably, master(s) will be provided with the same degrees of freedom as the associated surgical instrument assemblies 54 to provide the surgeon with telepresence, the perception that the surgeon is immediately adjacent to and immersed in the surgical site, and intuitiveness, the perception that the master(s) are integral with the instruments 54 so that the surgeon has a strong sense of directly and intuitively controlling instruments 54 as if they are part of his hands. Position, force, and tactile feedback sensors (not shown) may also be employed on instrument assemblies 54 to transmit position, force, and tactile sensations from the surgical instrument back to the surgeon's hands as he/she operates the telerobotic system. One suitable system and method for providing telepresence to the operator is described in U.S. patent application Ser. No. 08/517,053, filed Aug. 21, 1995, which has previously been incorporated herein by reference.

The monitor 94 will be suitably coupled to the viewing scope assembly such that an image of the surgical site is provided adjacent the surgeon's hands on surgeon console. Preferably, monitor 94 will display an image on a display that is oriented so that the surgeon feels that he or she is actually looking directly down onto the operating site. To that end, an image of the surgical instruments 54 appears to be located substantially where the operator's hands are located even though the observation points (i.e., the endoscope or viewing camera) may not be from the point of view of the image. In addition, the real-time image is preferably transformed into a stereo image such that the operator can manipulate the end effector and the hand control as if viewing the workspace in substantially true presence. By true presence, it is meant that the presentation of an image is a true stereo image simulating the viewpoint of an operator that is physically manipulating the surgical instruments 54. Thus, a controller (not shown) transforms the coordinates of the surgical instruments 54 to a perceived position so that the stereo image is the image that one would see if the camera or endoscope was located directly behind the surgical instruments 54. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

A servo control is provided for transferring the mechanical motion of masters to manipulator assemblies 51. The servo control may be separate from, or integral with manipulator assemblies 51. The servo control will usually provide force and torque feedback from the surgical instruments 51 to the hand-operated masters. In addition, the servo control may include a safety monitoring controller (not shown) to safely halt system operation or at least inhibit all robot motion in response to recognized undesirable conditions (e.g., exertion of excessive force on the patient, mismatched encoder readings, etc.). The servo control preferably has a servo bandwidth with a 3 dB cut off frequency of at least 10 hz so that the system can quickly and accurately respond to the rapid hand motions used by the surgeon and yet to filter out undesirable surgeon hand tremors. To operate effectively with this system, manipulator assemblies 51 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Referring now to FIGS. 2-6 in conjunction with FIGS. 1A-1C, an improved apparatus, system, and method for sensing and feedback of forces and/or torques to the surgeon will be described in accordance with an embodiment of the present invention.

Figure 2:
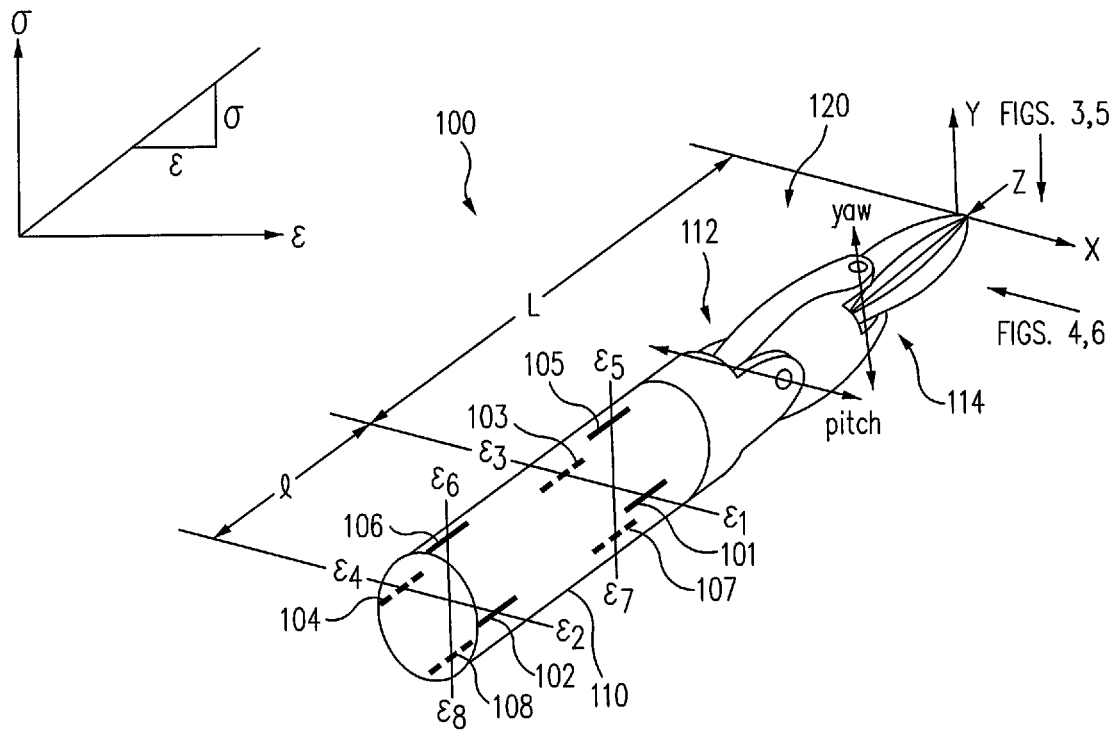
FIG. 2 is a perspective view of a surgical instrument distal end showing a wrist, grip jaws, and force sensor for use with a telerobotic surgical system in accordance with an embodiment of the present invention.

FIG. 2 shows a perspective view of a portion 100 of a surgical instrument including a shaft 110, wrist joints 112 and 114, and an end portion 120 that may be used to manipulate a surgical tool and/or contact the patient. The surgical instrument also includes a housing 150 (FIGS. 9A-9C) that operably interfaces with a robotic manipulator arm, in one embodiment via a sterile adaptor interface. Applicable housings, sterile adaptor interfaces, and manipulator arms are disclosed in U.S. patent application Ser. No. 11/314,040 and U.S. Provisional Application No. 60/752,755, both filed on Dec. 20, 2005, the full disclosures of which (including all references incorporated by reference therein) are incorporated by reference herein for all purposes. Applicable shafts, end portions, housings, sterile adaptors, and manipulator arms are available from Intuitive Surgical Inc. of Sunnyvale, Calif.

In a preferred configuration, end portion 120 has a range of motion that includes pitch and yaw motion, rotation about the z-axis, and actuation of an end effector, via cables through shaft 110 and housing 150 that transfers motion and electrical signals from the manipulator arm 51. Movement of end portion 120 along the x, y, and z axes may be provided by the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which (including disclosures incorporated by reference therein) are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are commercially available from Intuitive Surgical, Inc. of Sunnyvale, Calif.

In accordance with an embodiment of the present invention, instrument portion 100 includes sensors (e.g., strain gauges) mounted onto the exterior surface of shaft 110, oriented parallel to the axis of the shaft, termed the z-axis. The two axes perpendicular to the shaft are called the x- and y-axes. The signals from the sensors are combined arithmetically in various sums and differences (as will be explained in further detail below) to obtain measures of three perpendicular forces (e.g., $F_x$, $F_y$, and $F_z$) exerted upon the instrument tip and the torques about the two axes perpendicular to the shaft axis (Tx, Ty) (i.e., axes x and y). In accordance with the present invention, the measurement of the forces is made independent of the orientation and effective lever arm length of an articulated wrist mechanism at the distal end of the instrument. Forces exerted against end portion 120 are detected by the force sensing elements, which may be operably coupled to servo control via an interrogator or a processor for transmitting these forces to master(s).

In one embodiment, eight strain gauges 101, 102, 103, 104, 105, 106, 107, and 108 are mounted to the outer surface of shaft 110 or in shallow recesses near the outer surface and provide strain data $\epsilon_1$, $\epsilon_2$, $\epsilon_3$, $\epsilon_4$, $\epsilon_5$, $\epsilon_6$, $\epsilon_7$, and $\epsilon_8$, respectively. The primary strain sensing direction of the gauges are oriented parallel to the shaft lengthwise axis (z-axis). The gauges are mounted in two groups of four, wherein the four gauges in one group are spaced equally, 90 degrees apart around the circumference of the shaft at one axial position (i.e., forming two "rings" of strain gauges). One group of four (e.g., gauges 101, 103, 105, and 107) is mounted proximal to a wrist mechanism as close to a distal end of shaft 110 as possible. The second group of four (e.g., gauges 102, 104, 106, and 108) is mounted at a chosen distance "l" from the first group of four (toward a proximal end of shaft 110) and aligned with them so that pairs of gauges in the two groups are aligned with each other (e.g., gauges 101 and 102, 103 and 104, 105 and 106, and 107 and 108 are aligned).

The z-axis force ($F_z$) is found from the sum of the eight gauge outputs multiplied by a factor of EA/8, where E is the shaft material modulus of elasticity in the axial direction, and A is the cross-sectional area of the shaft. The lateral forces along the x- and y-axes ($F_x$ and $F_y$) at or near the tip are found from the difference of the gauge outputs of a pair of gauges on opposite sides of the shaft and the difference between the pair differences along the shaft multiplied by a factor of EI/2rl, where E is the shaft material modulus of elasticity in the axial direction, I is the shaft section moment of inertia, r is the radius from the shaft axis to the acting plane of the gauges, and l is the distance between the 2 groups of 4 gauges The calculations of the forces are derived from the following equations.

With respect to FIG. 2, $$E = \sigma/\varepsilon$$

$$A = \pi(r_o^2 - r_i^2)$$

$$I = (\pi/4)(r_o^4 - r_i^4)$$

$$\sigma = (F/A) + (Mr/I)$$

$$\varepsilon = [\varepsilon_1 \ \varepsilon_2 \ \varepsilon_3 \ \varepsilon_4 \ \varepsilon_5 \ \varepsilon_6 \ \varepsilon_7 \ \varepsilon_8]$$

$$\overset{F_x}{\begin{bmatrix} 1 \\ -1 \\ -1 \\ 1 \\ 0 \\ 0 \\ 0 \\ 0 \end{bmatrix}} EI/2lr \quad \overset{F_y}{\begin{bmatrix} 0 \\ 0 \\ 0 \\ 0 \\ 1 \\ -1 \\ -1 \\ 1 \end{bmatrix}} EI/2lr \quad \overset{F_z}{\begin{bmatrix} 1 \\ 1 \\ 1 \\ 1 \\ 1 \\ 1 \\ 1 \\ 1 \end{bmatrix}} - EA/8$$

Figure 3:
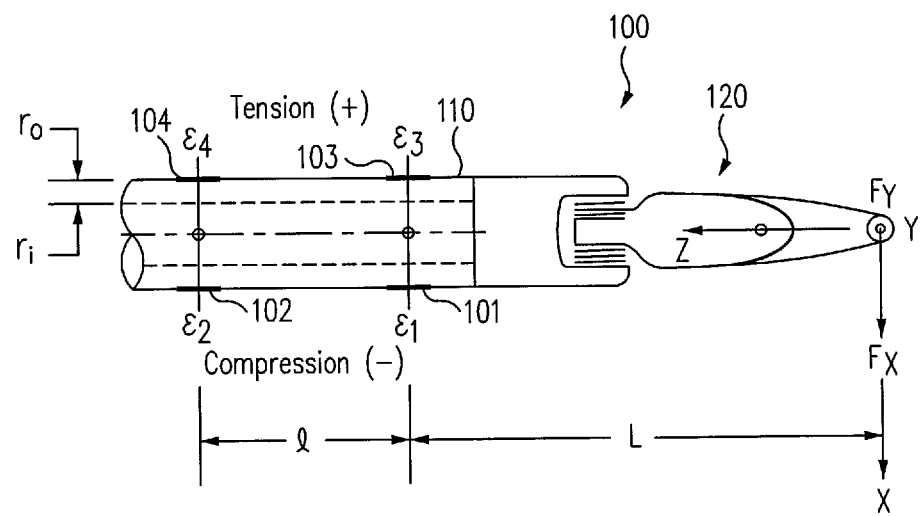
FIG. 3 is a first top view of the surgical instrument of FIG. 2 showing applied forces in accordance with the embodiment of the present invention.
Figure 4:
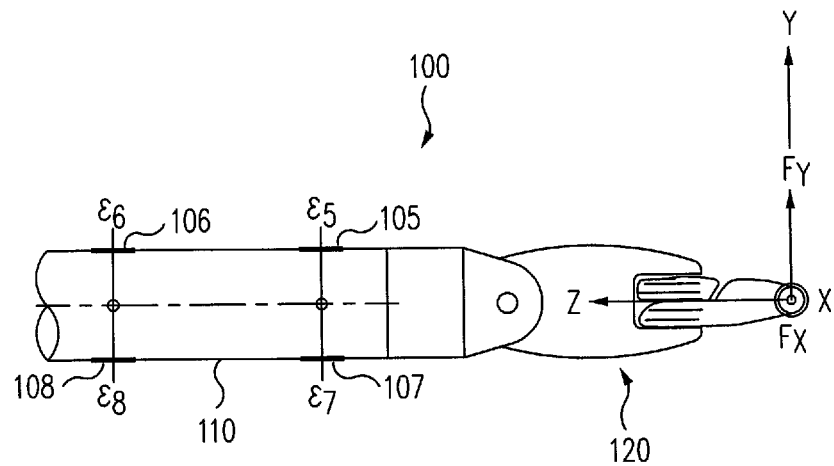
FIG. 4 is a first side view of the surgical instrument of FIG. 2 showing applied forces in accordance with the embodiment of the present invention.

With respect to FIGS. 3 and 4, $$A = \pi(r_o^2 - r_i^2)$$

$$I = (\pi/4)(r_o^4 - r_i^4)$$

$$\sigma = Mr/I$$

-continued $$\sigma_1 = FLr/I$$

$$\sigma_2 = F(L+l)r/I$$

$$E = \sigma/\varepsilon => \varepsilon = \sigma/E$$

$$\varepsilon_1 = -F_x Lr/EI$$

$$\varepsilon_2 = -F_x(L+l)r/EI$$

$$\varepsilon_2 - \varepsilon_1 = -F_x lr/EI$$

modulus of elasticity in the axial direction, I is the shaft section moment of inertia, and r is the radius from the shaft axis to the acting plane of the gauges. Thus the forces (Fx, Fy, Fz) and torques (Tx, Ty) exerted at the instrument tip are measured without errors due to wrist orientation or the location of a gripped tool such as a suture needle within jaws or tissue held in a grasper, for example. Torque measurements about the x- and y-axes are also independent of temperature at steady state. The calculations of the torques are derived from the following equations.

Figure 5:
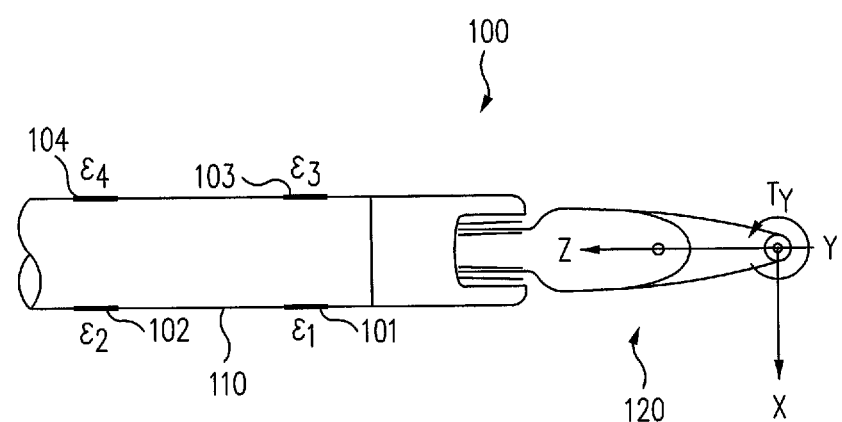
FIG. 5 is a second top view of the surgical instrument of FIG. 2 showing applied torque in accordance with the embodiment of the present invention.
Figure 6:
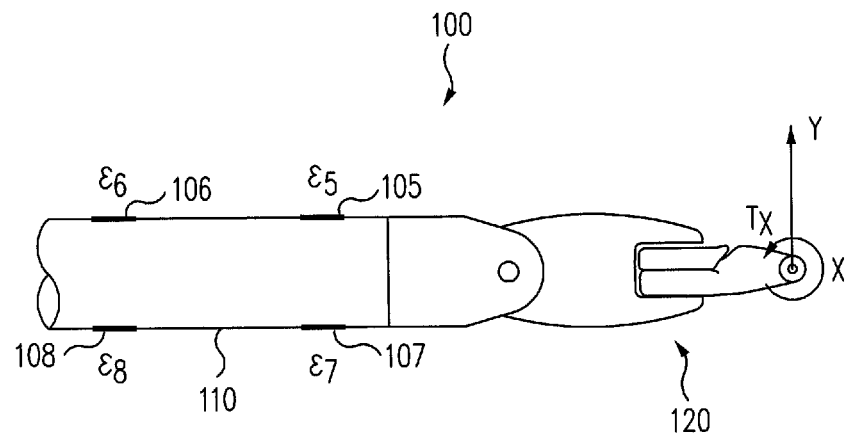
FIG. 6 is a second side view of the surgical instrument of FIG. 2 showing applied torque in accordance with the embodiment of the present invention.

With respect to FIGS. 5 and 6 in conjunction with FIG. 2, $$\begin{bmatrix} 0 \\ 0 \\ 0 \\ 0 \\ -1 \\ -1 \\ 1 \\ 1 \end{bmatrix} EI/4r \quad \begin{bmatrix} 1 \\ 1 \\ -1 \\ -1 \\ 0 \\ 0 \\ 0 \\ 0 \end{bmatrix} EI/4r$$

$$\sigma = Mr/I$$

$$\sigma_1 = \sigma_2 = Tr/I$$

$$E = \sigma/\varepsilon \Rightarrow \varepsilon = \sigma/E$$

$$\varepsilon_1 = \varepsilon_2 = Tr/EI$$

Thus, $$(\varepsilon_1 + \varepsilon_2 - \varepsilon_3 - \varepsilon_4)EI/4r = T_y$$
$$(-\varepsilon_5 - \varepsilon_6 + \varepsilon_7 + \varepsilon_8)EI/4r = T_x$$

-continued $$\varepsilon_4 - \varepsilon_3 = F_x lr/EI$$

$$(\varepsilon_4 - \varepsilon_3) - (\varepsilon_2 - \varepsilon_1) = 2F_x lr/EI$$

Thus, $$(\varepsilon_1 - \varepsilon_2 - \varepsilon_3 + \varepsilon_4)EI/2lr = F_x$$
$$(\varepsilon_5 - \varepsilon_6 - \varepsilon_7 + \varepsilon_8)EI/2lr = F_y$$
$$(\varepsilon_1 + \varepsilon_2 + \varepsilon_3 + \varepsilon_4 + \varepsilon_5 + \varepsilon_6 + \varepsilon_7 + \varepsilon_8)EA/8 = F_z$$

$F_x$ and $F_y$ are thus invariant with respect to L and invariant with respect to temperature at steady state.

Advantageously, the present invention makes the measured force at the instrument tip independent of variations in the effective lever arm length due to wrist orientation changes or gripping position changes in the end portion during surgery. In addition, the measured forces along the x- and y-axes are independent of temperature changes when at thermal equilibrium over all gauges. This may be seen by adding an equal temperature disturbance strain to all four gauges in the equations for $F_x$ and $F_y$ and noting that the disturbances cancel. Thermal transients during which gauge temperatures are unequal are not compensated by this design although other measures may be taken to do so.

The measurements of the torques about the x- and y-axes (Tx and Ty) at the instrument tip are derived from the differences of the gauges paired across the shaft diameter and the sum of the pair differences along the shaft axis multiplied by a factor EI/4r, wherein once again E is the shaft material While the invention described above may be applied to surgical instruments of many constructions, it is of particular value for use with anisotropic linear fiber reinforced polymer tubing, in one example, because all gauges are oriented parallel to the axis with constant and easily characterized elastic properties. Similar advantages may be gained with properly characterized woven reinforced tubing and the method is also applicable to uniform elastic property tubing.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft.

As an example, with no intention to limit the invention thereby, two commercially available fiber strain gauge technologies noted above will be described in greater detail.

The first employs a Fabry-Perot cavity formed by first fusing two fibers together so as to produce a half-mirror at the junction and then polishing the tip of the fiber so as to form a full mirror. Light is sent into the fiber to generate reflections from both the half-mirror and the full mirror. The two reflections generate interference patterns that are a function of the distance between the two mirrors, thus allowing the strain in the fiber to be sensed. This Fabry-Perot technology is commercially available from FISO Technologies Inc. of Quebec, Canada, with more information available at http://www.fiso.com.

The second technology uses a Bragg grating written into the fiber with a UV laser. The fiber Bragg grating (FBG) gauge comprises a spatial periodicity in the refractive index along the axis of the fiber. Light entering the FBG is preferentially reflected at a particular wavelength (the Bragg wavelength) that is a function of the period of the index variation. Other wavelengths pass through the FBG unchanged. To measure strain, broad spectrum IR light is sent down the fiber, and the wavelength of the reflection indicates the strain. This FBG technology is commercially available from Smart Fibres Ltd. of Bracknell, England, with more information available at http://www.smartfibres.com.

Multiple FBGs can be written into a fiber if they are formed in such a way as to use a different range of wavelengths, and as noted above, this is a particularly useful property for the double ring of strain gauges embodiment as only four fibers would need to be embedded into the instrument shaft, each with two FBGs separated by a known distance. To implement the double ring arrangement of strain gauges with the Fabry-Perot technology, eight fibers would be required.

Both fiber technologies require an interrogator unit that decodes the optically encoded strain information into electrical signals compatible with the computer control hardware of the robotic surgical system. A processor may then be used to calculate forces according to the equations outlined above in conjunction with the signals from the strain gauges/sensors. In one embodiment, an interrogator unit 170 (FIG. 9A) could be mounted on the manipulator, or elsewhere in the surgical system, which could require routing of the optical fiber across the sterile boundary. In one case, an optical coupling could be incorporated into the standard instrument interface with the manipulator such that installation of an instrument onto the manipulator automatically forms an optical link with the instrument. Advantageously this would avoid the need to carry external cabling to the instrument. In a second case, a fiber pigtail could exit the top of the instrument for mating with a connector presented on the manipulator but not part of the instrument interface. In these two cases, the interrogator could be built into the manipulator or fiber cables could run through the manipulator to an interrogator mounted on the surgical system or in the operating room separate from the manipulator. In a third case, a fiber pigtail could exit the top of the instrument without passing through the manipulator for mating with an interrogator unit mounted in the operating room separate from the manipulator, which has the benefit of not requiring connection of the fiber cable when the instrument is attached or removed from the manipulator.

Other combinations of gauge orientations, numbers of gauges, and outputs are also within the scope of the present invention. In accordance with another embodiment of the present invention, a useful simplification of the two ring eight gauge arrangement is to remove one of the rings of gauges. This simplification removes the ability to distinguish between forces and moments on a given axis (e.g., x or y), but many items in the surgical environment (e.g., human tissue, sutures) do not support moments well, and thus it is possible to assume that all strain information is from x and y-axis forces. In a further embodiment, three gauges 120 degrees apart may be used to form a set instead of four gauges 90 degrees apart. Thus, combinations of gauges may include a single ring of three gauges 120 degrees apart, two rings of three gauges each 120 degrees apart (i.e., a total of six gauges), a single ring of four gauges 90 degrees apart, and two rings of four gauges each 90 degrees apart (i.e., a total of eight gauges). Single ring gauge embodiments may be useful for non-wristed tools such as probes. Gauges may also be oriented on the surface of shaft 110 at angles that permit recovery of the additional torque signal $T_z$ about the shaft axis. However, the off-axis elastic properties must be taken into account.

In accordance with yet another embodiment of the present invention, x- and y-axis forces may be detected with sensor(s) at the distal end of the instrument shaft as disclosed above, and z-axis forces may be detected with a sensor(s) located outside of the body near the proximal end of the instrument. Various sensors may be used outside of the body for detecting z-axis forces, including but not limited to strain gauges and/or fiber technologies.

Typically, z-axis forces cannot be easily sensed at the instrument tip because the instrument shaft is subject to significant internal forces in the z-direction from the internal cabling necessary for transmitting torques to the instrument pitch and yaw axes. These cables run inside the instrument shaft and experiments have shown that the compression loads on the shaft vary significantly as the instrument is operated. Attempts to sense z direction strain with gauges on the instrument shaft will include a significant cabling "noise" in addition to the applied z-axis force of interest. Thus, it is preferred that z-axis forces be sensed in a location substantially not subject to internal cabling forces. It is noted that these cables also impart some x- and y-moments at the base of the shaft because the cables are not completely centered and because cable tension on either side of the wrist pulleys will vary as the wrist is operated. However, experiments have shown that, unlike the z-direction cable forces, these variations are relatively small compared to the expected externally applied forces.

Z-axis forces however may be detected outside the body with relative accuracy with mainly the cannula seal friction and sliding friction of the shaft in the cannula adding "noise" to the signal of interest. In one embodiment, cannula seals are disposable and may be packaged with lubrication, and in another embodiment, the instrument shaft surfaces may be treated with friction reducing coatings (e.g., PTFE) to negate undesirable friction noise. Both methods may also be used simultaneously. A sensor may be placed in various locations outside of the body proximate the proximal end of the surgical instrument in accordance with the present invention. It is preferred that the sensor be built into the manipulator rather than the disposable instrument but this is not necessarily so. In one embodiment, a sensor(s) 160 (FIG. 9A) may be used at mount points for the instrument sterile adaptor on the manipulator arm insertion (Z-axis) carriage. In another embodiment, the input/output axis pulleys in the instrument housing/carriage may be mounted on a sensor(s), allowing for the detection of force applied to the I/O axis by the I/O motor. However, this placement would also introduce the additional frictional noise associated with the I/O axis itself. In yet another embodiment, a sensor(s) may be placed at the instrument backplate. This would be substantially equivalent to placing sensors on the sterile adaptor mount points but would require an additional sensor be built into every instrument.

By contrast to the Z-axis forces, the X- and y-axis forces cannot easily be sensed outside the body because of the large body-wall forces and torques imparted to the instrument at the remote center that mask the comparatively small x- and y-axis tissue contact forces. Thus, it is preferred that x- and y-axis forces be sensed in a location substantially not subject to body-wall forces or torques such as the distal end of the instrument shaft proximal to the instrument wrist joint as discussed above. In the disclosure above, a force-torque sensor integrated with the tubular distal end of an endoscopic surgical instrument shaft is described. In one embodiment, the sensor is comprised of two sets of four strain gauges located about the periphery of the shaft such that the members of a group of four are 90 degrees apart around the shaft and the two groups of four are a distance l apart along the shaft. In one aspect, it was desired to determine the side load (e.g., $F_y$) on the instrument tip or jaws. The disclosure explains that by computing the bending moment at each group of sensors due to the side load and then subtracting the two values, a measure of the side load independent of wrist orientation and resulting effective lever arm length can be derived. A concern is that the moments applied to the distal end of the shaft by the actuation of the instrument wrist axes and transmitted to the shaft by the friction in the wrist pivots will interfere with the intended measurement of the side loads. However, by carrying the terms due to such moments through the arithmetic governing the measured strains, it may be seen that the terms due to such moments drop out when the side load forces are calculated.

Figure 7:
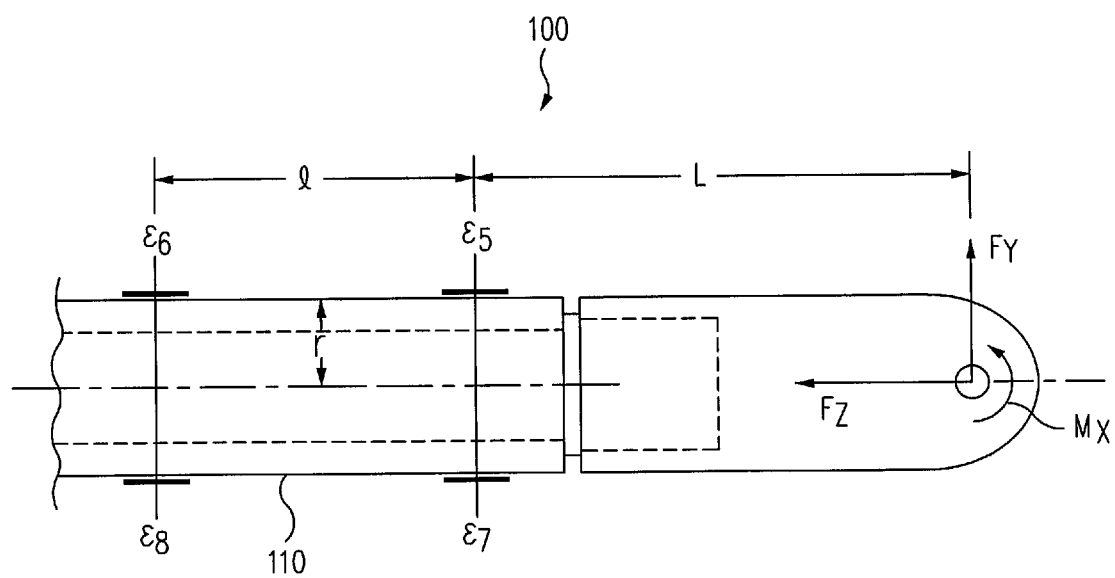
FIG. 7 shows a free body diagram of the instrument shaft and proximal wrist clevis subjected to loads and moments applied by the wrist mechanism in accordance with an embodiment of the present invention.
Figure 8:
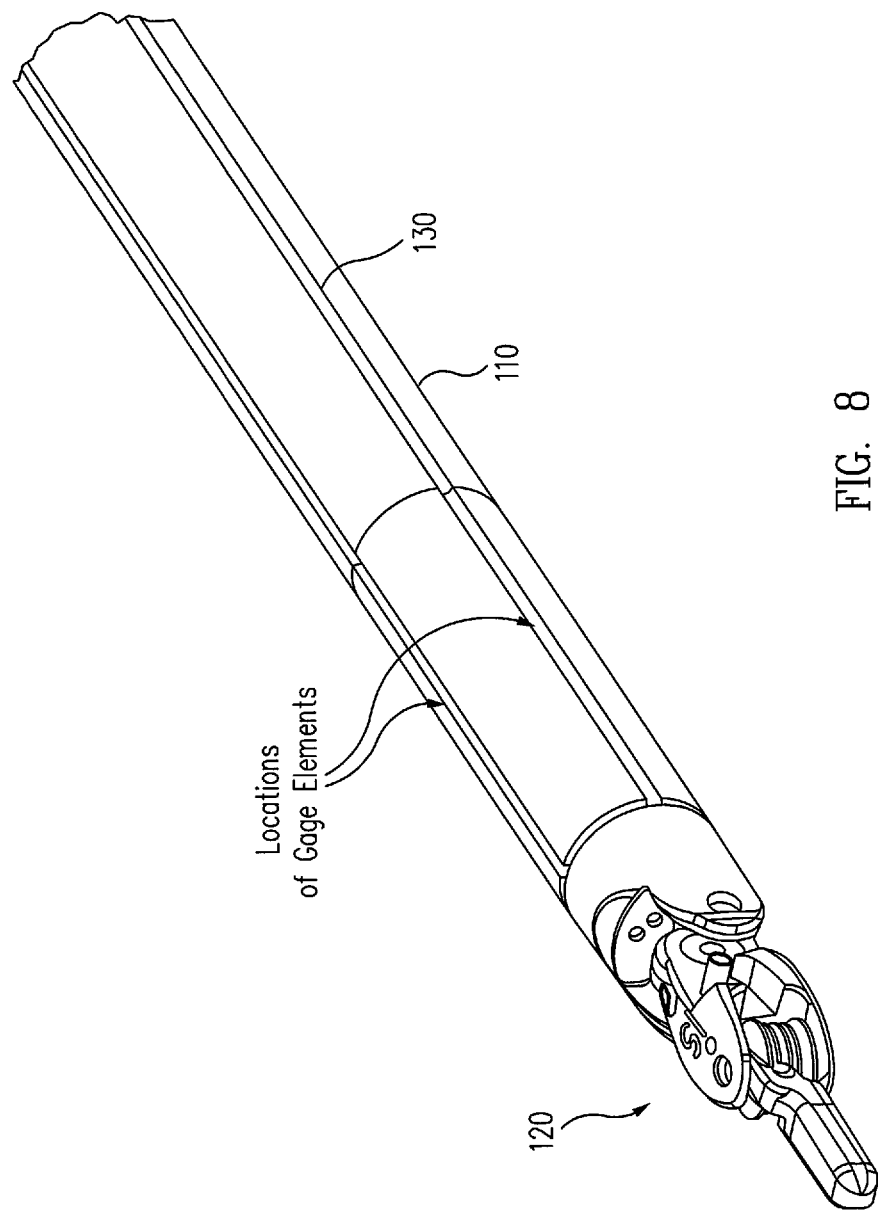
FIG. 8 shows a grooved instrument shaft for embedded strain gauges in accordance with an embodiment of the present invention.

Referring now to FIG. 7 and the equations below, by proper arithmetic combination of the strains sensed by the eight strain gauges, it is possible to eliminate the unwanted axial wrist cable forces and wrist actuation torques while preserving the desired side load forces. FIG. 7 illustrates a free body diagram of the shaft subjected to loads and moments applied by the wrist mechanism. While a variety of combinations of forces and moments may apply to the free body of the outboard wrist itself depending on the combination of tip loads, cable loads, and motion and acceleration of the wrist, the forces and moment applied to the end of the shaft viewed in the Y-Z plane and the reference frame of the shaft always reduce to $F_y$ (side load), $F_z$ (axial load), and $M_x$ (wrist pivot friction moment load).

Therefore, one can express the strains $\epsilon_5$, $\epsilon_6$, $\epsilon_7$, and $\epsilon_8$ on the four gauges in this plane in terms of these three loads and derive the expression for the desired side force $F_y$ as follows.

Tensile strain > 0

Compressive strain < 0

$$\varepsilon_7 = -F_z/EA + M_x r/EI + F_y Lr/EI$$

$$\varepsilon_5 = -F_z/EA - M_x r/EI - F_y Lr/EI$$

$$\varepsilon_8 = -F_z/EA + M_x r/EI + F_y(1+L)r/EI$$

$$\varepsilon_6 = -F_z/EA - M_x r/EI - F_y(1+L)r/EI$$

$$[(\varepsilon_8 - \varepsilon_6) - (\varepsilon_7 - \varepsilon_5)] = -F_z/EA[(1-1)-(1-1)] + M_x r/EI$$
$$[(1-(-1))-(1-(-1))] +$$
$$F_y r/EI\{[(1+L)-(-(1+L))] - [L-(-L)]\}$$
$$= 2lF_y r/EI$$

Therefore, $$\boxed{F_y = [(\varepsilon_8 - \varepsilon_6) - (\varepsilon_7 - \varepsilon_5)]EI/2lr}$$

$M_x$ and $F_z$ do not appear.

As can be seen, the strains due to the moment load $M_x$ which are felt identically on both sets of gauges drop out leaving the moment loads due to the applied side force $F_y$. The strain components due to the axial force $F_z$ also felt identically on both sets of gauges also drop out. Therefore, since the wrist actuating torques are transmitted to the shaft carrying the strain sensors by the friction in the wrist joint, they result in moment loads that cancel when the signals from the two sets of sensors are subtracted, leaving a relatively clean signal due to the side force load alone as desired. The above disclosure similarly applies to $\epsilon_{1-4}$ in the x-z plane with x and y interchanged.

Calculating a clean signal due substantially to the side force load alone advantageously eliminates the need to place the sensor outboard of (distal to) the wrist joints as previously done to eliminate the wrist friction moments. The present invention thus avoids the need to route wires or optic fibers associated with the strain gauges through the flexing wrist joint. Furthermore, the yaw and grip axes may be accomplished on the same pivot axis rather than having them separate as previously done.

For all of the methods and apparatus mentioned above, it may be advantageous to use a calibration process in which combinations of forces and torques are applied to the instrument tip serially, simultaneously, or in combinations while correction factors and offsets are determined to apply to the theoretical equations for combining the gauge outputs to obtain $F_x$, $F_y$, $F_z$, $T_x$, and $T_y$. This calibration may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Figure 9A:
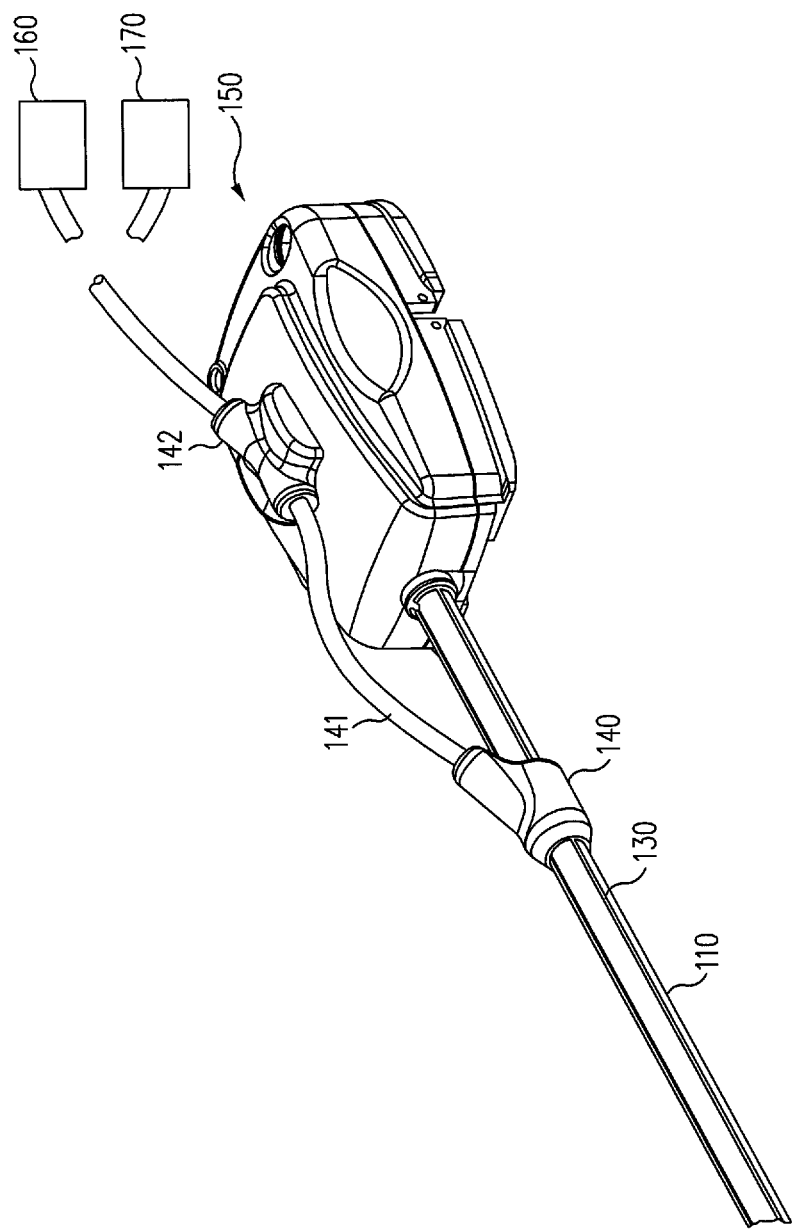
FIGS. 9A-9C show different configurations of a strain relief and service loop for strain gauge wires or optic fibers in accordance with an embodiment of the present invention.
Figure 9B:
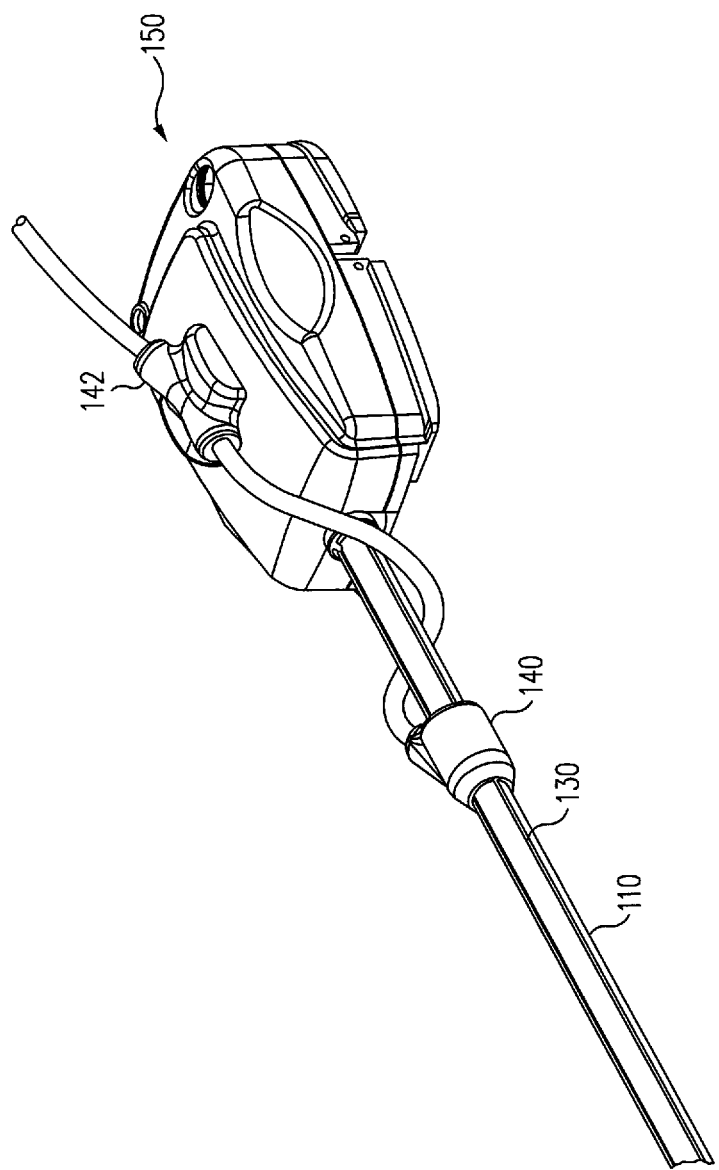
Figure 9C:
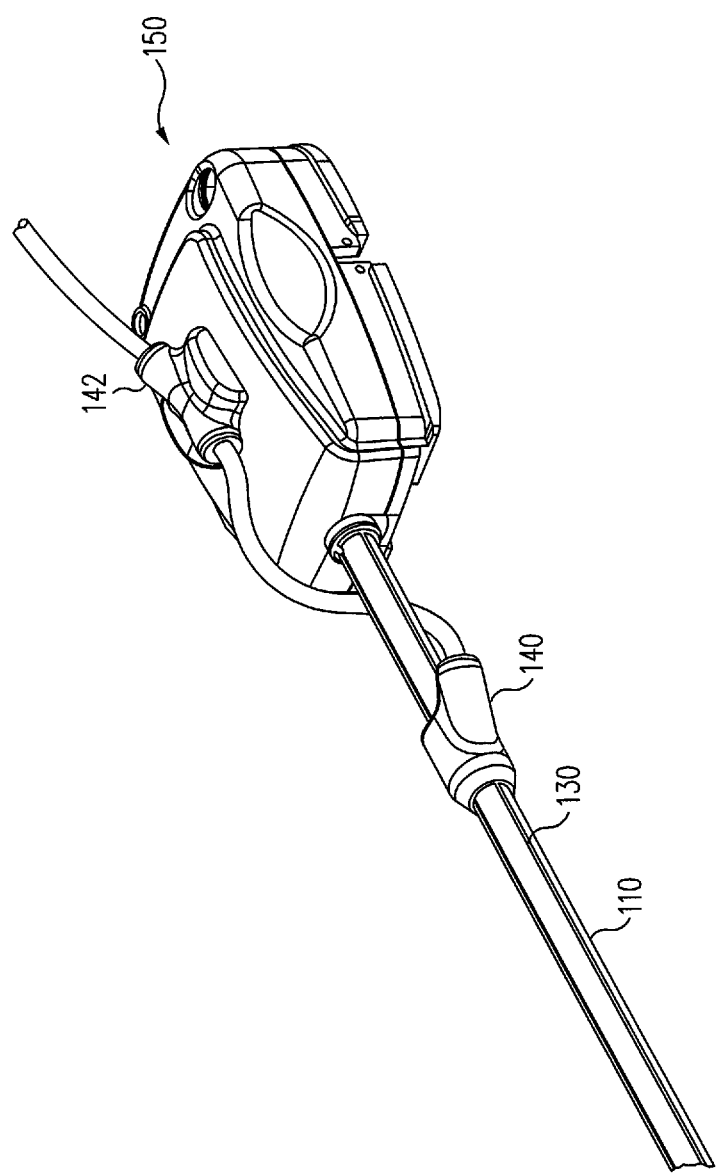

Optical fibers embedded in the instrument shaft preferably should exit the shaft near the proximal end of the instrument in a way that does not impede rotation of the shaft relative to the instrument housing/carriage while preserving the physical integrity of the fiber. Referring now to FIGS. 8 and 9A-9C, in accordance with an embodiment of the present invention, Fabry-Perot or FBG sensing elements may be embedded in shallow grooves 130 just below the shaft 110 surface near the instrument shaft distal tip just behind the wrist clevis, and then epoxied or otherwise potted into place. Grooves 130 may lead back toward the proximal end of the instrument which includes the motion inputs and wrist cable actuator mechanism (the "housing") 150. Grooves 130 may be formed in the shaft during the initial pultrusion process or the grooves may be machined after shaft production. At a point near the proximal mechanism or housing, the fibers may be routed out of the grooves at a gentle angle and bundled through a strain relief 140 into a protective flexible sheath 141 which would carry the optical fibers to a strain relieved anchor point 142 on the top cover of the mechanism housing 150. The flexible sheath 141, strain relief 140, and anchor point 142 should have sufficient length and flexibility to permit safe repeated flexing and torsion as the instrument shaft 110 is rotated through a plus/minus three-quarter turn roll axis range of motion, as shown in FIGS. 9A-9C.

In another embodiment, if the instrument shaft is made with resin and fiber (e.g., fiberglass or carbon fiber), the optical fibers may be woven or embedded with linear axial reinforcing fibers at the desired angular (90 or 120 degrees) and radial (near surface) positions into the instrument shaft fiber matrix prior to the application of resin.

Advantageously, the present invention eliminates undesirable interference from wrist actuator cable tensions ($F_z$) and wrist actuation moments ($M_x$) with the desired sensing of the tip side load ($F_y$) by combining strain measurements and locating the sensors inboard of the wrist pitch and yaw axes. Accordingly, wires or optic fibers are not required to pass through the wrist joints, thereby avoiding possible signal loss, breakage of wires or fibers, interfering noise, and/or current leakage (fiber optics do not require current and provide no leakage path) while insuring greater reliability and simpler less expensive construction. The use of fiber strain gauges advantageously provide immunity to electrical and magnetic fields, which become an issue with cautery tools that generate large currents and voltages, while also providing bio-compatibility, durability to withstand temperatures and pressures associated with autoclaving, and size advantages. Furthermore, the wrist yaw and grip axes may share the same pivot shaft and actuator cables operated differentially for yaw and in common mode for grip thus simplifying and reducing the cost of the assembly while increasing its reliability. In addition, the combined overall length of the wrist and end effector may be kept to a minimum reducing the side offset distance when the wrist is bent.

Embodiments described above illustrate but do not limit the invention. It should also be understood that numerous modifications and variations are possible in accordance with the principles of the present invention. For example, the number of strain gauges and their configuration may vary but must allow for applicable force and torque determinations. In yet another example, strain gauges may be non-uniformly offset in a ring, such as by 60 degrees and 120 degrees. Accordingly, the scope of the invention is defined only by the following claims.

We claim:

1. A surgical instrument, comprising:
a housing portion configured to operably interface with a manipulator arm of a robotic surgical system;
a shaft including: a proximal end coupled to the housing portion, a distal end, a distal end portion extending proximally from the distal end, and a lengthwise axis defined from the proximal end to the distal end;
a plurality of strain gauges mounted on the distal end portion of the shaft adjacent to the distal end of the shaft;
a wrist joint operably coupled to the distal end of the shaft, wherein the plurality of strain gauges do not extend to any movable element in the wrist joint; and
an instrument tip operably coupled to the wrist joint, wherein articulation of the wrist joint moves the instrument tip in at least one degree of freedom, and wherein the plurality of strain gauges are configured to measure at least one force acting on the instrument tip.

2. The instrument of claim 1,
wherein the shaft includes a plurality of grooves in an outer surface of the shaft,
wherein the grooves extend along the lengthwise axis of the shaft, and
wherein the plurality of strain gauges are mounted in the grooves.

3. The instrument of claim 1, wherein the plurality of strain gauges includes eight strain gauges in two groups of four, with each of the strain gauges in a group being spaced apart by 90 degrees around the shaft.

4. The instrument of claim 1, wherein the plurality of strain gauges includes six strain gauges in two groups of three, with each of the strain gauges in a group being spaced apart by 120 degrees around the shaft.

5. The instrument of claim 1, wherein the plurality of strain gauges includes four strain gauges spaced apart by 90 degrees around the shaft.

6. The instrument of claim 1, wherein the plurality of strain gauges includes three strain gauges spaced apart by 120 degrees around the shaft.

7. The instrument of claim 1, wherein each strain gauge is aligned with one other strain gauge along an axis parallel to the shaft lengthwise axis.

8. The instrument of claim 1, wherein the plurality of strain gauges are positioned proximal of pitch and yaw axes of the wrist joint.

9. The instrument of claim 1, wherein the primary strain sensing direction of each of the strain gauges is oriented parallel to the shaft lengthwise axis.

10. The instrument of claim 1, wherein the plurality of strain gauges is selected from a group consisting of fiber optic, foil, surface acoustic wave, and semiconductor type strain gauges.

11. The instrument of claim 1, wherein a strain gauge is selected from a group consisting of a Fabry-Perot strain gauge and a fiber Bragg grating strain gauge.

12. The instrument of claim 1, wherein the plurality of strain gauges includes at least two fiber Bragg gratings along one fiber.

13. The instrument of claim 1, wherein a grip axis of the distal end portion is the same as a yaw axis of the wrist joint.

14. The instrument of claim 1, wherein the instrument tip of the surgical instrument is selected from a group consisting of jaws, scissors, graspers, needle holders, micro-dissectors, staple appliers, tackers, suction irrigation tools, clip appliers, cutting blades, cautery probes, irrigators, catheters, and suction orifices.

15. The instrument of claim 1, wherein the housing portion interfaces with a sterile adaptor of a sterile drape covering the manipulator arm.

16. The instrument of claim 1, wherein the housing portion optically links to the manipulator arm.

17. The instrument of claim 1, further comprising a force sensor proximate the housing portion for sensing an axial force along the lengthwise axis of the shaft.

18. The instrument of claim 1, further comprising an integrated circuit storing calibration data for a surgical instrument force sensor.

19. The instrument of claim 1, further comprising a rotatable strain relief operably coupled to a proximal end of the shaft for routing a plurality of fibers off the shaft at an angle from the lengthwise axis of the shaft.

20. A robotic surgical system, comprising:
a manipulator assembly including a manipulator arm; and
a surgical instrument operably coupled to the manipulator arm, the surgical instrument including:
a housing portion for operably interfacing with the manipulator arm;
a shaft including: a proximal end coupled to the housing portion, a distal end, a tubular distal end portion extending proximally from the distal end, and a lengthwise axis defined from the proximal end to the distal end;
a plurality of strain gauges mounted on the distal end portion of the shaft adjacent to the distal end of the shaft;
a wrist joint operably coupled to the distal end of the shaft, wherein the plurality of strain gauges do not extend to any movable element in the wrist joint, and wherein articulation of the wrist joint moves the instrument tip in at least one degree of freedom; and
an instrument tip operably coupled to the wrist joint, wherein the plurality of strain gauges are configured to measure at least one force acting on the instrument tip.

21. The system of claim 20, wherein the manipulator arm is a patient side manipulator arm or an endoscope camera manipulator arm.

22. The system of claim 20,
wherein the shaft includes a plurality of grooves in an outer surface of the shaft,
wherein the grooves extend along the lengthwise axis of the shaft, and wherein the plurality of strain gauges are mounted in the grooves.

23. The system of claim 20, wherein the plurality of strain gauges includes eight strain gauges in two groups of four, with each of the strain gauges in a group being spaced apart by 90 degrees around the shaft.

24. The system of claim 20, wherein the plurality of strain gauges includes six strain gauges in two groups of three, with each of the strain gauges in a group being spaced apart by 120 degrees around the shaft.

25. The system of claim 20, wherein the plurality of strain gauges includes four strain gauges spaced apart by 90 degrees around the shaft.

26. The system of claim 20, wherein the plurality of strain gauges includes three strain gauges spaced apart by 120 degrees around the shaft.

27. The system of claim 20, wherein each strain gauge is aligned with one other strain gauge along an axis parallel to the shaft lengthwise axis.

28. The system of claim 20, wherein the plurality of strain gauges are positioned proximal of pitch and yaw axes of the wrist joint.

29. The system of claim 20, wherein the primary strain sensing direction of each of the strain gauges is oriented parallel to the shaft lengthwise axis.

30. The system of claim 20, wherein the plurality of strain gauges is selected from a group consisting of fiber optic, foil, surface acoustic wave, and semiconductor type strain gauges.

31. The system of claim 20, wherein a strain gauge is selected from a group consisting of a Fabry-Perot strain gauge and a fiber Bragg grating strain gauge.

32. The system of claim 20, wherein the plurality of strain gauges includes at least two fiber Bragg gratings along one fiber.

33. The system of claim 20, wherein a grip axis of the distal end portion is the same as a yaw axis of the wrist joint.

34. The system of claim 20, wherein the instrument tip of the surgical instrument is selected from a group consisting of jaws, scissors, graspers, needle holders, micro-dissectors, staple appliers, tackers, suction irrigation tools, clip appliers, cutting blades, cautery probes, irrigators, catheters, and suction orifices.

35. The system of claim 20, wherein the housing portion interfaces with a sterile adaptor of a sterile drape covering the manipulator arm.

36. The system of claim 20, wherein the housing portion optically links to the manipulator arm.

37. The system of claim 20, further comprising a force sensor proximate the housing portion for sensing an axial force along the lengthwise axis of the shaft.

38. The system of claim 20, further comprising a force sensor on the manipulator arm for sensing an axial force along the lengthwise axis of the shaft.

39. The system of claim 20, further comprising a processor configured to calculate a first force based upon at least a sum of signals from the plurality of strain gauges and a second force based upon at least a difference of signals from a pair of strain gauges, in the plurality of strain gauges, on opposite sides of the shaft.

40. The system of claim 20, wherein the surgical instrument further comprises an integrated circuit storing calibration data for a surgical instrument force sensor.

41. The system of claim 20, wherein the surgical instrument further comprises a rotatable strain relief operably coupled to a proximal end of the shaft for routing a plurality of fibers off the shaft at an angle from the lengthwise axis of the shaft.

* * * * *